United States Patent
Ishaque et al.

(10) Patent No.: US 9,125,411 B2
(45) Date of Patent: Sep. 8, 2015

(54) UV ABSORBERS FOR REDUCING THE E/Z ISOMERIZATION OF PESTICIDES

(75) Inventors: Michael Ishaque, Mannheim (DE); Vijay Narayanan Swaminathan, Mumbai (IN); Sylke Haremza, Neckargemünd (DE); Claude Taranta, Stutensee (DE); William Baxter, Releigh, NC (US)

(73) Assignee: BASF SE, Ludwigshafen (DE)

( * ) Notice: Subject to any disclaimer, the term of this patent is extended or adjusted under 35 U.S.C. 154(b) by 30 days.

(21) Appl. No.: 13/085,781

(22) Filed: Apr. 13, 2011

(65) Prior Publication Data

US 2011/0257265 A1   Oct. 20, 2011

Related U.S. Application Data

(60) Provisional application No. 61/324,339, filed on Apr. 15, 2010.

(51) Int. Cl.
*A01N 47/34* (2006.01)

(52) U.S. Cl.
CPC ...................... *A01N 47/34* (2013.01)

(58) Field of Classification Search
None
See application file for complete search history.

(56) References Cited

U.S. PATENT DOCUMENTS

| | | | |
|---|---|---|---|
| 4,171,355 | A | 10/1979 | Stubbs et al. |
| 4,259,189 | A | 3/1981 | Li |
| 4,926,190 | A | 5/1990 | Laver |
| 4,973,702 | A | 11/1990 | Rody et al. |
| 6,395,776 | B1 | 5/2002 | Losel et al. |
| 2004/0062728 | A1 | 4/2004 | Boutelet et al. |
| 2006/0041038 | A1 | 2/2006 | Xia |
| 2006/0194057 | A1 | 8/2006 | Pfluecker et al. |
| 2011/0237665 | A1 | 9/2011 | Misske et al. |

FOREIGN PATENT DOCUMENTS

| | | |
|---|---|---|
| CA | 2 006 418 | 6/1990 |
| CA | 2 091 064 | 3/1992 |
| DE | 19 14 059 | 10/1970 |
| DE | 195 28 529 | 2/1997 |
| DE | 10333029 | 2/2005 |
| EP | 0 057 160 | 6/1985 |
| EP | 0 280 650 | 8/1988 |
| EP | 0 376 888 | 7/1990 |
| EP | 0 513 902 | 11/1992 |
| EP | 0496106 | 12/1995 |
| EP | 0 845 942 | 10/2002 |
| EP | 1 401 832 | 2/2005 |
| JP | 4 198 148 | 7/1992 |
| WO | WO 92/03926 | 3/1992 |
| WO | WO 97/42815 | 11/1997 |
| WO | WO 03/063814 | 8/2003 |
| WO | WO 2004/052327 | 6/2004 |
| WO | WO 2005/015993 | 2/2005 |
| WO | WO2005/047235 | * 5/2005 |
| WO | WO 2005/072680 | 8/2005 |
| WO | WO 2006/077394 | 7/2006 |
| WO | WO 2006/089747 | 8/2006 |
| WO | WO 2008/085682 | 7/2008 |
| WO | WO 2009/153231 | 12/2009 |
| WO | WO 2010/063657 | 6/2010 |
| WO | WO 2010/103021 | 9/2010 |

OTHER PUBLICATIONS

Hussain, M., et al., "The Effect of Selected UV Absorber Compounds on the Photodegradation of Pyrethroid Insecticides Applied to Cotton Fabric Screens", Pesticide Science, (1990), pp. 345-355, vol. 28.
Kuehr et al., Titanium dioxide photoinduced degradation of some pesticide/fungicide precursors, Pest Management Science, 2007, vol. 63, pp. 491-494.
Miskus et al., Stabilization of thin films of pyrethrins and allethrin, Journal of Agricultural and Food Chemistry, 1972, vol. 20, pp. 313-315.
Philippon, A. et al., "Macrocyclic Ethers by Free Radical Cyclizations", Synthetic Communications, (1997), pp. 2651-2682, vol. 27.
Topalov et al., Photocatalytic Oxidation of the Fungicide Metalaxyl Dissolved in Water over TiO2, Water Research, 1999, vol. 33, pp. 1371-1376.
Office Action dated Jun. 20, 2012 in related U.S. Appl. No. 12/999,912.
Office Action dated Feb. 29, 2012 in related U.S. Appl. No. 12/999,912.
European Search Report prepared in corresponding European Application No. 10160057, (2010).
Hu, Ji Ye et al., "Photodegradation of Flumorph in Aqueous Solutions and Natural Water under Abiotic Conditions", J. Agric. Food Chem., 2009, pp. 9629-9633, vol. 57, No. 20.
Takagi, K. et al., "Discovery of metaflumizone, a novel semicarbazone insecticide", Veterinary Parasitology, 2007, pp. 177-181, vol. 150.
Basf, "Uvinul grades. UV absorbers for cosmetic products", Technical Information BASF, Aug. 1995, pp. 1-21.
Waldeck, D.H., "Photoisomerization Dynamics of Stilbenes", Chem. Rev. 1991, pp. 415-436, vol. 91.
Wyman, G.M., "The *Cis-Trans* Isomerization of Conjugated Compounds", Chem. Rev. 1955, pp. 625-657.
Ideses, Rut, et al., "Chemical protection of pheromones containing an internal conjugated diene system form isomerization and oxidation", Journal of Chemical Ecology, 1988, p. 1657-1669, vol. 14, No. 8.
"Sumisorb 300 for use in crop protection", National Organic Standards Board Technical Advisory Panel Review, Apr. 3, 2003, pp. 1-14.
"Z-COTE and T-Lite™ microfine pigments for broad spectrum UV protection", Nov. 17, 2005, pp. 1-44, XP 55104876.

* cited by examiner

*Primary Examiner* — Bong-Sook Baek
(74) *Attorney, Agent, or Firm* — Brinks Gilson & Lione

(57) ABSTRACT

The present invention provides the use of a UV absorber for reducing the E/Z isomerization of pesticides comprising a double bond. It furthermore relates to a composition comprising an E and/or a Z isomer of a pesticide comprising a double bond and a UV absorber.

6 Claims, No Drawings

UV ABSORBERS FOR REDUCING THE E/Z ISOMERIZATION OF PESTICIDES

The present patent document claims the benefit of the filing date under 35 U.S.C. §119 (e) of U.S. Provisional Patent Application Ser. No. 61/324,339, filed Apr. 15, 2010, which is hereby incorporated by reference.

The present invention provides the use of a UV absorber for reducing the E/Z isomerization of pesticides comprising a double bond. It furthermore relates to a composition comprising an E and/or a Z isomer of a pesticide comprising a double bond and a UV absorber. Combinations of preferred features with other preferred features are included in the present invention.

Agrochemical active compounds such as pesticides are particularly exposed to solar irradiation after application in the open. In the case of some active compounds, this leads to a reduction in their pesticidal activity.

Thus, it has been found that, for example, metaflumizone loses activity by irradiation by light (Takagi et al., Veterinary Parasitology, 2007, 150, 177-181). Metaflumizone can exist as the E and as the Z isomer, the E isomer having an up to 10-fold higher pesticidal activity than the Z isomer. By irradiation by light, isomerization of the E isomer originally applied to the Z isomer occurs.

The object was achieved by the use of a UV absorber for reducing the E/Z isomerization of pesticides comprising a double bond.

E/Z isomerization is conventionally understood as meaning the conversion of a double bond from the E isomer into the Z isomer or from the Z isomer into the E isomer. E/Z isomerization usually occurs with unsymmetrically substituted double bonds, i.e. with double bonds which can exist as the E isomer and as the Z isomer. Aromatic double bonds such as are present in benzene rings of course cannot undergo E/Z isomerization. A reduction in E/Z isomerization is conventionally achieved if the weight ratio of E to Z isomer in a composition changes more slowly compared with the same composition without the particular UV absorber employed.

The term pesticide designates at least one active compound chosen from the group of fungicides, insecticides, nematicides, herbicides, safeners, pheromones and/or growth regulators. Preferred pesticides are fungicides, insecticides and herbicides. Mixtures of pesticides from two or more of the abovementioned classes can also be used. The person skilled in the art is familiar with such pesticides, which can be found, for example, in Pesticide Manual, 15th Ed. (2009), The British Crop Protection Council, London. Suitable insecticides are insecticides from the class of carbamates, organophosphates, organochlorine insecticides, phenylpyrazoles, pyre-

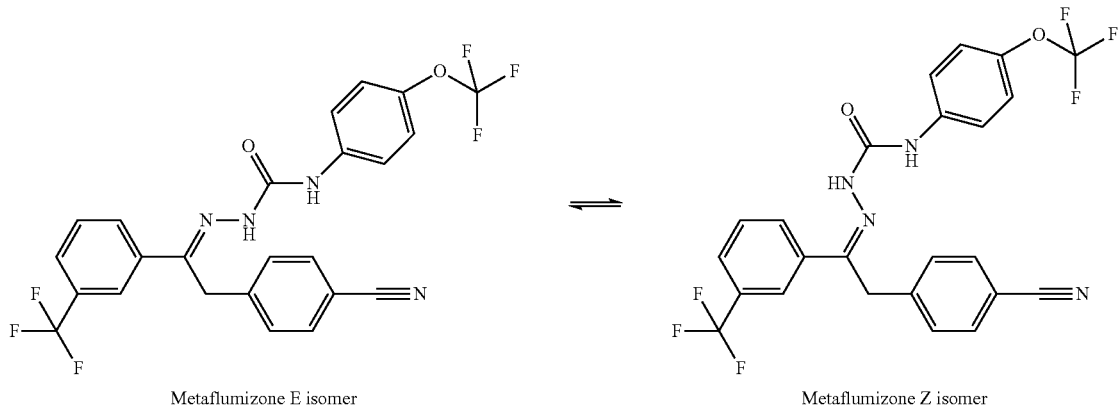 [SMILES: N#Cc1ccc(C/C(=N\NC(=O)Nc2ccc(OC(F)(F)F)cc2)c2cccc(C(F)(F)F)c2)cc1 ; N#Cc1ccc(C/C(=N/NC(=O)Nc2ccc(OC(F)(F)F)cc2)c2cccc(C(F)(F)F)c2)cc1]

Metaflumizone E isomer ⇌ Metaflumizone Z isomer

A similar E/Z isomerization is known for flumorph (Hu et al., J. Agricul. Food Chem. 2009, 57, 9629-9633).

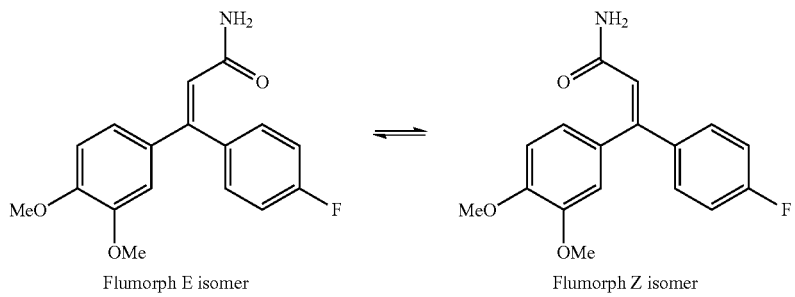 [SMILES: COc1ccc(/C(=C/C(N)=O)c2ccc(F)cc2)cc1OC ; COc1ccc(/C(=C\C(N)=O)c2ccc(F)cc2)cc1OC]

Flumorph E isomer ⇌ Flumorph Z isomer

An object of the present invention was to suppress the E/Z isomerization of agrochemical active compounds, such as metaflumizone. A further object was to find an inexpensive process for this.

throids, neonicotinoids, spinosins, avermectins, milbemycins, juvenile hormone analogs, alkyl halides, organotin compounds, nereistoxin analogs, benzoylureas, diacylhydrazines, METI acaricides, and insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenone, or derivatives thereof. Suitable fungicides are fungicides of the classes dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amides, chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazolecarboxamides, guanidines, hydroxy-(2-amino)-pyrimidines, hydroxyanilides, imidazoles, imidazolinones, inorganic compounds, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides of the classes of acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolinones, triazolocarboxamides, triazolopyrimidines, triketones, uracils, ureas.

Pesticides comprising a double bond are conventionally those pesticides which comprise a C—C double bond and/or a C—N double bond. The double bond is usually isolated from another multiple bond or conjugated to another multiple bond.

Preferred pesticides comprising a double bond are abamectin, acetamiprid, acrinathrin, azoxystrobin, bifenthrin, butoxycarboxim, chlorfenvinfos, cyhalothrin, 1,3 dichloropropene, dicrotophos, dimethomorph, diniconazole, emamectin, empenthrin, fenpyroximate, flucycloxuron, flumethrin, flumorph, fluoxastrobin, hydroprene, kinoprene, kresoxime-methyl, lambda-cyhalothrin, metaflumizone, metominostrobin, metoprene, mevinphos, monocrotophos, nitenpyram, oxabetrinil, phosphamidon, picoxystrobin, propetamphos, pyrethrin, pyrifenox, tefluthrin, tetrachlorvinphos, trifloxystrobin, triflumizole, triticonazole, uniconazole, and the pheromones codlemon, dodec-8-enyl acetate, dodec-9-enyl acetate, dodeca-7,9-dienyl acetate, farnesol, nerolidol, gossyplure, grandlure II, grandlure III, hexadec-11-enal, hexadec-11-enyl acetate, hexadec-13-en-11-ynyl acetate, japonilure, muscalure, tetradeca-9,12-dienyl acetate, tetradeca-11-enyl acetate, tetradeca-9-enyl acetate and tridec-4-enyl acetate.

Particularly preferred pesticides comprising a double bond are abamectin, acetamiprid, azoxystrobin, bifenthrin, cyhalothrin, dimethomorph, diniconazole, emamectin, flucycloxuron, fluoxastrobin, kresoxim-methyl, lambda-cyhalothrin, metaflumizone, picoxystrobin, trifloxystrobin, triflumizole and triticonazole.

Metaflumizone is a specifically preferred pesticide comprising a double bond.

In a further preferred embodiment, pesticides comprising a double bond wherein the E or the Z isomer of the pesticide has a higher activity than the other particular isomer are suitable. The expression "higher activity" in each case relates to a certain biological activity on a certain target organism. These activities of the E and the Z isomers of the pesticide are usually known from the literature. A higher activity is present if one of the isomers has an activity which is at least 1.1 times (preferably at least 2 times, particularly preferably at least 4 times) the activity of the other isomer.

The E or the Z isomer of the pesticide comprising a double bond is preferably present in an amount to at least 60 wt. %, preferably to at least 75 wt. %, particularly preferably to at least 90 wt. %, based on the total amount of the E and Z isomers of the pesticide. These values relate to the point in time when the UV absorber is mixed with the pesticide.

The expression "UV absorber" relates to all chemical compounds which can absorb UV light. The UV absorber can scatter UV light (like inorganic UV absorbers) or absorb it. The extinction coefficient of the UV absorber of UV light is usually greater than the extinction coefficient of the pesticide at the same wavelength. The UV absorbers can be oil-soluble or water-soluble. They can also be bonded into polymers, for example as copolymerized. The UV absorbers can be UV-A absorbers, UV-B absorbers, broad band absorbers (i.e. UV-A and UV-B) or optical brighteners. The UV absorbers can be employed in the pure form, as a technical grade mixture or as a mixture of various UV absorbers. Preferred UV absorbers have a solubility in water at 20° C. of at least 0.01 g/l, preferably at least 0.1 g/l and particularly preferably at least 1 g/l.

In a preferred embodiment, the UV absorber is water-soluble. In a further preferred embodiment, the composition comprises a further UV absorber, the further UV absorber being oil-soluble. In particular, at least one UV absorber is water-soluble and at least one UV absorber is oil-soluble.

In a particularly preferred embodiment, suitability is possessed by water-soluble UV absorbers having a solubility in water at 20° C. of at least 5.0 g/l, preferably at least 10.0 g/l, particularly preferably at least 50 g/l, and especially at least 100 g/l.

The further, oil-soluble UV absorber has typically a solubility in water at 20° C. of below 5.0 g/l, preferably below 1.0 g/l, particularly preferably below 0.5 g/l, and especially below 0.1 g/l. Inorganic UV absorbers are likewise suitable oil-soluble UV absorbers for the purposes of this application.

Suitable UV absorbers are, for example,

A) benzotriazoles, such as 2-(2H-benzotriazol-2-yl)-4,6-bis(1-methyl-1-phenylethyl)phenol (Tinuvin® 900, BASF SE), [3-[3-(2H-benzotriazol-2-yl)-5-(1,1-dimethylethyl)-4-hydroxyphenyl]-1-oxopropyl]-w-[3-[3-(2H-benzotriazol-2-yl)-5-(1,1-dimethylethyl)-4-hydroxyphenyl]-1-oxopropoxy]poly(oxy-1,2-ethanediyl) (Tinuvin® 1130, BASF SE), 6-tert-butyl-2-(5-chloro-2H-benzotriazol-2-yl)-4-methylphenol (Tinuvin® 326, BASF SE), 2,4-di-tert-butyl-6-(5-chloro-2H-benzotriazol-2-yl)-phenol (Tinuvin® 327, BASF SE), 2-(2H-benzotriazol-2-yl)-4,6-di-tert-pentylphenol (Tinuvin® 320, BASF SE), 2-(2H-benzotriazol-2-yl)-4-(1,1,3,3-tetramethylbutyl)-phenol (Tinuvin® 329, BASF SE), 2-(2H- benzotriazol-2-yl)-4-methylphenol (Tinuvin® P, BASF SE), 2-(2H-benzotriazol-2-yl)-4,6-bis(1-methyl-1-phenylethyl)phenol (Tinuvin® 234, BASF SE), 2,2'-methylenebis(6-(benzotriazol-2-yl)-4-tert-octylphenol (Tinuvin® 360, BASF SE); 2-(2H-benzotriazol-2-yl)-2-(2-methylpropyl)phenol-4-sulfonic acid sodium salt (Tinogard H® P, BASF SE), phenol, 2-(2H-benzotriazol-2-yl)-6-dodecyl-4-methyl-, branched and linear (Tinuvin® 171, BASF SE);

B) cyanoacrylates, such as 2-cyano-3-phenylcinnamate ethyl ester (Uvinul® 3035, BASF SE), 2-cyano-3,3-diphenylacrylic acid 2'-ethylhexyl ester or 2-ethylhexyl 2-cyano-3-phenylcinnamate (octocrylene, Uvinul® 539 T, Uvinul 3039, BASF SE);

C) para-aminobenzoic acid (PABA) derivatives, in particular esters, such as ethyl PABA, ethoxylated PABA, ethyl dihydroxypropyl-PABA, glycerol-PABA, 2-ethylhexyl 4-(dimethylamino)benzoate (Uvinul® MC 80), 2-octyl 4-(dimethylamino)benzoate, amyl 4-(dimethylamino) benzoate, 4-bis(polyethoxy)-4-aminobenzoic acid polyethoxyethyl ester (Uvinul® P 25, BASF SE);

D) esters of salicylic acid, such as 2-ethylhexyl salicylate, 4-isopropylbenzyl salicylate, homomethyl salicylate, TEA salicylate (Neo Heliopan® TS, Haarmann and Reimer), dipropylene glycol salicylate;

E) esters of cinnamic acids, such as 2-ethylhexyl 4-methoxycinnamate (Uvinul® MC 80), octyl p-methoxycinnamate, propyl 4-methoxycinnamate, isoamyl 4-methoxycinnamate, cinoxate, diisopropyl methylcinnamate, etocrylene (Uvinul® N 35, BASF SE);

F) derivatives of benzophenone, such as 2-hydroxy-4-methoxybenzophenone (Uvinul® M 40, BASF SE), 2-hydroxy-4-methoxy-4'-methylbenzophenone, 2,2'-dihydroxy-4-methoxybenzophenone, 2-(4-diethylamino-2-hydroxybenzoyl)-benzoic acid hexyl ester (Uvinul® A Plus, BASF SE), 4-n-octyloxy-2-hydroxy-benzophenone (Uvinul® 3008, BASF SE), 2-hydroxybenzophenone derivatives, such as 4-hydroxy-, 4-methoxy-, 4-octyloxy-, 4-decyloxy-, 4-dodecyloxy-, 4-benzyloxy-, 4,2',4'-trihydroxy-, 2'-hydroxy-4,4'-dimethoxy-2-hydroxybenzophenone, sulfonic acid derivatives of benzophenones, such as 2-hydroxy-4-methoxybenzophenone-5-sulfonic acid (Uvinul® MS 40, BASF SE) and its salts, 2,2'-dihydroxy-4,4'-dimethoxybenzophenone-5,5'-sulfonic acid and its salts (disodium salt: Uvinul® DS 49, BASF SE);

G) 3-benzylidenecamphor and derivatives thereof, such as 3-(4'-methylbenzylidene)d-1-camphor, benzylidenecamphorsulfonic acid (Mexoryl® SO, Chimex);

H) sulfonic acid derivatives of 3-benzylidenecamphor, such as 4-(2-oxo-3-bornylidenemethyl)benzenesulfonic acid and 2-methyl-5-(2-oxo-3-bornylidene)sulfonic acid and salts thereof;

I) esters of benzalmalonic acid, such as 2-ethylhexyl 4-methoxybenzalmalonate;

J) triazine derivatives, such as dioctylbutamidotriazone (Uvasorb® HEB, Sigma), 2,4,6-trianilino-p-(carbo-2'-ethyl-hexyl-1'-oxy)-1,3,5-triazine (Uvinul® T 150, BASF SE), 2-[4-[(2-hydroxy-3-(2'-ethyl)hexyl)oxy]-2-hydroxyphenyl]-4,6-bis(2,4-dimethylphenyl)-1,3,5-triazine (Tinuvin® 405, BASF SE), anisotriazine (Tinosorb® S, BASF SE), 2,4,6-tris(diisobutyl 4'-aminobenzalmalonate)-s-triazine;

K) propane-1,3-diones, such as 1-(4-tert-butylphenyl)-3-(4'-methoxyphenyl)propane-1,3-dione;

L) 2-phenylbenzimidazole-5-sulfonic acid or 2-phenylbenzimidazole-4-sulfonic acid and alkali metal, alkaline earth metal, ammonium, alkylammonium, alkanolammonium and glucammonium salts thereof;

M) derivatives of benzoylmethane, such as 1-(4'-tert-butylphenyl)-3-(4'-methoxyphenyl)-propane-1,3-dione, 4-tert-butyl-4'-methoxydibenzoylmethane or 1-phenyl-3-(4'-isopropylphenyl)-propane-1,3-dione;

N) amino-hydroxy-substituted derivatives of benzophenones, such as N,N-diethylamino-hydroxybenzoyl-n-hexyl-benzoate;

O) derivatives of stilbene, for example salts of distyrylbiphenyldisulfonate, such as disodium distyrylbiphenyldisulfonate (Uvitex® NFW, BASF SE), 2,2'-[1,2-ethenediylbis[(3-sulfo-4,1-phenylene)imono-[6-(diethylamino)-1,3,5-triazine-4,2-diyl]imino]]-bis-1,4-benzenedisulfonic acid hexasodium salt (Tinopal® SFP, BASF SE);

P) inorganic UV absorbers, for example those based on ZnO (such as Z-Cote® products, BASF SE), TiO$_2$ (such as T-Lite™ products, BASF SE) or CeO$_2$, and the UV absorbers as described in WO 2009/153231, page 2, line 24 to page 6, line 18.

Preferred UV absorbers are those of group F) (derivatives of benzophenone) and group O) (derivatives of stilbene), particularly preferably 2-hydroxybenzophenone derivatives, sulfonic acid derivatives of benzophenones and salts of distyrylbiphenyldisulfonate, in particular 2-hydroxy-4-methoxybenzophenone, 2-hydroxy-4-methoxybenzophenone-5-sulfonic acid, disodium distyrylbiphenyldisulfonate and 2-hydroxy-4-octoxybenzophenones.

In a further preferred embodiment, at least two UV absorbers are used. In this context a UV absorber from group A) to N) and a UV absorber from group O) are preferably employed.

In a particularly preferred embodiment, UV absorbers are used which comprise a sulfonic acid group or a polyalkylene oxide group. Preference is given to UV absorbers which comprise a sulfonic acid group.

UV absorbers which comprise a sulfonic acid group are common knowledge. Examples are 2-hydroxy-4-methoxybenzophenone-5-sulfonic acid (Uvinul® MS 40, BASF SE) and its salts (e.g. alkali metal salt, such as sodium), 2,2'-dihydroxy-4,4'-dimethoxybenzo-phenone-5,5'-sulfonic acid and its salts (e.g. alkali metal salt, such as sodium). Preference is given to benzophenones which comprise a sulfonic acid group (also called sulfonic acid derivative of benzophenones). The sulfonic acid group may be present in the acid form or as a salt, the salt form being preferred.

UV absorbers which comprise a polyalkylene oxide group are common knowledge. The polyalkylene oxide group preferably comprises ethylene oxide in polymerized form. Preferably at least 50 mol %, in particular at least 80 mol %, of the alkylene oxide groups are ethylene oxide. Examples are 4-bis(polyethoxy)-4-aminobenzoic acid polyethoxyethyl esters (Uvinul® P 25, BASF SE).

The amount of UV absorber is usually 0.5 to 500 wt. % with respect to the amount of the pesticide. It is preferably 1 to 300 wt. %, particularly preferably 5 to 100 wt. % and in particular 5 to 80 wt. %, in each case with respect to the amount of the pesticide.

In a preferred embodiment, an antioxidizing agent (also called antioxidant) is used in addition to the UV absorber. Preferred antioxidants have a solubility in water at 20° C. of at least 0.01 g/l, preferably at least 0.1 g/l and particularly preferably at least 1 g/l. In a further preferred embodiment, suitable antioxidants have a solubility in water at 20° C. of at least 5.0 g/l, preferably at least 20 g/l, and particularly preferably at least 100 g/l.

Antioxidants are, for example, amino acids (e.g. glycine, histidine, tyrosine, tryptophan) and derivatives thereof, imidazole and imidazole derivatives (e.g. urocanic acid), peptides, such as e.g. D,L-carnosine, D-carnosine, L-carnosine and derivatives thereof (e.g. anserine), carotenoids, carotenes (e.g. α-carotene, β-carotene, lycopene) and derivatives thereof, liponic acid and derivatives thereof (e.g. dihydroliponic acid), aurothioglucose, propylthiouracil and further thio compounds (e.g. thioglycerol, thiosorbitol, thioglycolic acid, thioredoxin, glutathione, cysteine, cystine, cystamine and glycosyl, N-acetyl, methyl, ethyl, propyl, amyl, butyl, lauryl, palmitoyl, oleyl, γ-linoleyl, cholesteryl and glyceryl esters thereof) as well as salts thereof, dilauryl thiodipropionate, distearyl thiodipropionate, thiodipropionic acid and derivatives thereof (esters, ethers, peptides, lipids, nucleotides, nucleosides and salts) as well as sulfoximine compounds (e.g. buthionine sulfoximine, homocysteine sulfoximine, buthionine sulfones, penta-, hexa-, heptathionine sulfoximine) in very low tolerable dosages, furthermore metal chelators (e.g. α-hydroxy-fatty acids, EDTA, EGTA, phytic acid, lactoferrin), α-hydroxy acids (e.g. citric acid, lactic acid, malic acid), humic acid, bile acid, bile extracts, gallic acid esters (e.g. propyl, octyl and dodecyl gallate), flavonoids, catechols, bilirubin, biliverdin and derivatives thereof, unsaturated fatty acids and derivatives thereof (e.g. γ-linolenic acid, linoleic acid, arachidonic acid, oleic acid), folic acid and derivatives thereof, hydroquinone and derivatives thereof (e.g. arbutin), ubiquinone and ubiquinol and derivatives thereof, Vitamin C and derivatives thereof (e.g. ascorbyl palmitate, stearate, dipalmitate, acetate, Mg ascorbyl phosphates, sodium and magnesium ascorbate, disodium ascorbyl phosphate and sulfate, potassium ascorbyl tocopheryl phosphate, chitosan ascorbate), isoascorbic acid and derivatives thereof, tocopherols and derivatives thereof (e.g. tocopheryl acetate, linoleate, oleate and succinate, tocophereth-5, tocophereth-10, tocophereth-12, tocophereth-18, tocophereth-50, tocophersolan), vitamin A and derivatives (e.g. vitamin A palmitate), the coniferylbenzoate of benzoin resin, rutin, rutic acid and derivatives thereof, disodium rutinyl disulfate, cinnamic acid and derivatives thereof (e.g. ferulic acid, ethyl ferulate, coffeic acid), gallic acid and its esters, for example propyl gallate, kojic acid, chitosan glycolate and salicylate, butylhydroxytoluene, butylhydroxyanisole, tetrakis[methylene(3,5-di-t-butyl-4-hydroxyhydrocinnamate)]-methane (Irganox® 1010, BASF SE), nordihydroguaiac resin acid, nordihydroguaiaretic acid, trihydroxybutyrophenone, uric acid and derivatives thereof, mannose and derivatives thereof, zinc and zinc derivatives (e.g. ZnO, $ZnSO_4$), selenium and selenium derivatives (e.g. selenium methionine), stilbenes and stilbene derivatives (e.g. stilbene oxide, trans-stilbene oxide), salts of monovalent copper, for example copper(I) chloride, bis(2,2,6,6-tetramethyl-4-piperidinyl) sebacate (Tinuvin® 770), 2-(2H-benzotriazol-2-yl)-6-dodecyl-4-methyl-phenol (Tinuvin® 171), N,N'-bisformyl-N,N'-bis-(2,2,6,6-tetramethyl-4-piperidinyl)-hexamethylenediamine (Uvinul® 4050 H, BASF SE).

Preferred antioxidants are vitamin C and derivatives thereof, tocopherols and derivatives thereof, salts of monovalent copper, bis(2,2,6,6-tetramethyl-4-piperidinyl) sebacate (Tinuvin® 770), 2-(2H-benzotriazol-2-yl)-6-dodecyl-4-methylphenol (Tinuvin® 171), N,N'-bisformyl-N,N'-bis-(2,2,6,6-tetramethyl-4-piperidinyl)-hexamethylenediamine (Uvinul® 4050 H, BASF SE).

The weight ratio of UV absorber to antioxidizing agent is usually in the range of from 1/10 to 100/1, preferably in the range of from 1/5 to 10/1, particularly preferably in the range of from 1/1 to 5/1.

The present invention furthermore relates to a composition comprising an E and/or a Z isomer of a pesticide comprising a double bond and a UV absorber. Suitable and preferred pesticides comprising a double bond are described above. The E isomer or the Z isomer of the pesticide is usually present in an amount to at least 60 wt. %, preferably to at least 75 wt. %, particularly preferably to at least 90 wt. %, based on the total amount of the E and Z isomers of the pesticide. That isomer which has the higher pesticidal activity is preferably present in excess.

Suitable UV absorbers are as described above. The UV absorber is preferably a derivative of benzophenone or a derivative of stilbene. In a further preferred embodiment, at least two UV absorbers are used. Suitable weight ratios of UV absorber to pesticide, which is metaflumizone, are as described above. In addition to the UV absorber, an antioxidizing agent as described above can be used.

The E isomer of metaflumizone is usually present in an amount to at least 60 wt. %, preferably to at least 75 wt. %, particularly preferably to at least 90 wt. %, based on the total amount of the E and Z isomers of metaflumizone.

The pesticides, such as metaflumizone, are typically present in composition types conventional for agrochemical formulations, e.g. solutions, emulsions, suspensions, dusts, powders, pastes and granules. The type depends on the particular intended use; it should in all cases ensure a fine and uniform distribution of the compound according to the invention. Examples of composition types are suspensions (SC, OD, OESC), emulsifiable concentrates (EC), emulsions (EW, EO, ES), pastes, pastilles, capsules (CS), wettable powders or dusts (WP, SP, SS, WS, DP, DS) or granules (GR, FG, GG, MG), which can be either soluble or dispersible in water, or LLIN (long-lasting insecticidal nets), baits for animals, such as ants or rats. The baits can be present in various of the abovementioned composition types, preferably as powders, pastes, granules or gels. In general the composition types (e.g. SC, EC, OD, WG, SG, WP, SP, SS, WS) are employed in diluted form. Composition types such as DP, DS, GR, FG, GG, MG or baits are as a rule employed in undiluted form. Preferred composition types are suspensions.

In a preferred embodiment, aqueous composition types are suitable, such as aqueous suspension concentrates, or oil-containing suspension concentrates (OESC). The pH of the aqueous composition types is typically greater than 1.0, preferably greater than 3.0 and particularly preferably greater than 3.5. The pH is usually below 6.0, preferably below 5.0 and particularly preferably below 4.5. Suitable ranges for the pH are, for example, 2.5 to 5.5, preferably 3.0 to 5.0.

The UV absorber and/or the antioxidants can already be brought into contact with the pesticide during preparation of the agrochemical formulation.

The agrochemical formulations can furthermore also comprise auxiliaries conventional for plant protection compositions, the choice of the auxiliaries depending on the concrete use form or the active compound. Examples of suitable auxiliaries are solvents, solid carrier substances, surface-active substances (such as further solubilizing agents, protective colloids, wetting agents and adhesive agents), organic and inorganic thickeners, bactericides, antifreeze agents, defoamers, optionally dyestuffs and adhesives (e.g. for seed treatment) or conventional auxiliaries for bait formulation (e.g. attractants, feedstuffs, bitters).

Possible solvents are water, organic solvents, such as mineral oil fractions of medium to high boiling point, such as kerosene and diesel oil, furthermore coal tar oils and oils of plant or animal origin, aliphatic, cyclic and aromatic hydrocarbons, e.g. paraffins, tetrahydronaphthalene, alkylated naphthalenes and derivatives thereof, alkylated benzenes and derivatives thereof, alcohols, such as methanol, ethanol, propanol, butanol and cyclohexanol, glycols, ketones, such as cyclohexanone, gamma-butyrolactone, dimethyl-fatty acid amides, fatty acids and fatty acid esters and strongly polar solvents, e.g. amines, such as N-methylpyrrolidone. In principle, solvent mixtures can also be used, as well as mixtures of the abovementioned solvents and water.

Solid carrier substances are mineral earths, such as silicas, silica gels, silicates, talc, kaolin, limestone, lime, chalk, bolus, loam, clay, dolomite, diatomaceous earth, calcium sulfate and magnesium sulfate, magnesium oxide, ground plastics, fertilizers, such as ammonium sulfate, ammonium phosphate, ammonium nitrate, ureas and plant products, such as cereal flour, tree bark, wood and nutshell flour, cellulose powder or other solid carrier substances.

Possible surface-active substances (adjuvants, wetting, adhesive, dispersing or emulsifying agents) are the alkali metal, alkaline earth metal and ammonium salts of aromatic sulfonic acids, e.g. of lignin- (Borresperse® types, Borregaard, Norway), phenol-, naphthalene- (Morwet® types, Akzo Nobel, USA) and dibutylnaphthalene-sulfonic acid (Nekal® types, BASF, Germany), and of fatty acids, alkyl- and alkylarylsulfonates, alkyl, lauryl ether and fatty alcohol sulfates, and salts of sulfated hexa-, hepta- and octadecanols, as well as of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctyl-, octyl- or nonylphenol, alkylphenyl or tributylphenyl polyglycol ethers, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetate, sorbitol esters, lignin-sulfite waste liquors and proteins, denatured proteins, polysaccharides (e.g. methylcellulose), hydrophobically modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone and copolymers thereof.

Examples of thickeners (i.e. compounds which impart to the composition modified flow properties, i.e. high viscosity in the resting state and low viscosity in the agitated state) are polysaccharides and organic and inorganic laminar minerals, such as xanthan gum (Kelzan®, CP Kelco, USA), Rhodopol® 23 (Rhodia, France) or Veegum® (R.T. Vanderbilt, USA) or Attaclay® (Engelhard Corp., NJ, USA).

Bactericides can be added to stabilize the composition. Examples of bactericides are those based on dichlorophen and benzyl alcohol hemiformal as well as isothiazolinone derivatives, such as alkylisothiazolinones and benzisothiazolinones (Acticide® MBS from Thor Chemie).

Examples of suitable antifreeze agents are ethylene glycol, propylene glycol, urea and glycerol.

Examples of defoamers are silicone emulsions (such as e.g. Silikon® SRE, Wacker, Germany or Rhodorsil®, Rhodia, France), long-chain alcohols, fatty acids, salts of fatty acids, organofluorine compounds and mixtures thereof.

The agrochemical formulations can be used in the form of their compositions, e.g. in the form of directly sprayable solutions, powders, suspensions, dispersions, emulsions, oil dispersions, pastes, dust compositions, scattering compositions or granules, by spraying, misting, dusting, scattering, laying out of baits, brushing, dipping or pouring.

Aqueous use forms can be prepared from emulsion concentrates, pastes or wettable powders (spray powders, oil dispersions) by addition of water. For the preparation of emulsions, pastes or oil dispersions, the substances can be homogenized in water as such or as a solution in an oil or solvent, by means of wetting, adhesive, dispersing or emulsifying agents. However, concentrates comprising wetting, adhesive, dispersing or emulsifying agent and possibly solvent or oil which are suitable for dilution with water can also be prepared from the active substance.

Oils of various types, wetting agents, adjuvants, herbicides, bactericides, other fungicides and/or pest control agents can be added to the active compounds or the compositions comprising these, optionally also only immediately before use (i.e. as a tank mix). These agents can be admixed to the compositions in the weight ratio of 1:100 to 100:1, preferably 1:10 to 10:1.

The UV absorber and/or the antioxidants can also be brought into contact with the pesticide only immediately before use (i.e. as a tank mix).

Possible adjuvants in this context are, in particular: organically modified polysiloxanes, e.g. Break Thru S 240®; alcohol alkoxylates, e.g. Atplus® 245, Atplus® MBA 1303, Plurafac® LF 300 and Lutensol® ON 30; EO-PO block polymers, e.g. Pluronic® RPE 2035 and Genapol® B; alcohol ethoxylates, e.g. Lutensol® XP 80; and sodium dioctyl sulfosuccinate, e.g. Leophen® RA.

The active compound concentrations in the ready-to-use formulations can be varied within relatively wide ranges. In general, they are between 0.0001 and 10%, preferably between 0.01 and 1%. The amounts applied for use in plant protection are between 0.01 and 2.0 kg of active compound per ha, depending on the nature of the desired effect. In the treatment of plant propagation materials, e.g. seed, in general active compound amounts of from 1 to 1000 g/100 kg, preferably 5 to 100 g/100 kg of propagation material or seed are used. For use in the protection of materials or stored products, the amount of active compound applied depends on the nature of the field of use and of the desired effect. Conventional amounts applied in the protection of materials are, for example, 0.001 g to 2 kg, preferably 0.005 g to 1 kg of active compound per cubic meter of material treated.

The present invention furthermore relates to a method of controlling phytopathogenic fungi and/or undesirable plant growth and/or undesirable insect or mite infestation and/or of regulating plant growth, wherein the composition according to the invention is allowed to act on the particular pests, their habitat or the plants to be protected from the particular pest, the soil and/or on the undesirable plants and/or the crop plants and/or their habitat.

The present invention has the most diverse advantages: The rate of E/Z isomerization is reduced significantly. The isomer applied remains active for longer in sunlight. As a result, the application rate of the active compound, such as metaflumizone, can be reduced. The active compound applied has a significantly longer residual action because the more active isomer applied is converted more slowly into the less active isomer. The practical conversion of the invention can be easily converted industrially, since the UV absorber can easily be brought into contact with the pesticide during preparation of the agrochemical formulation, or immediately before use by the user as a tank mix. By the addition of antioxidants, the action of the UV absorber for reduction of E/Z isomerization can be increased further. Water-soluble UV absorbers are particularly advantageous since such compositions are very storage stable, and can also easily be added by the user as a tank mix (since the absorber dissolves readily and is uniformly distributed in the aqueous tank mix). Water-soluble UV absorbers can be incorporated more easily into the formulation, since they are easily added to the aqueous formulation, whereas, for example, water-insoluble UV absorbers have to be additionally ground together with the active compound.

The following examples illustrate the invention without limiting it.

EXAMPLES

Metaflumizone SC: aqueous suspension concentrate comprising 240 g/l (22.2 wt. %) of metaflumizone, 2 wt. % of sodium dioctyl sulfosuccinate, 3.5 wt. % of ethoxylated $C_9$-$C_{11}$ alcohol and 3 wt. % of polyarylphenol ethoxylate.
UV absorbers employed (all commercially obtainable from BASF SE):
Uvitex® NFW: 4,4'-bis(2-sulfostyryl)-biphenyl disodium salt
Uvinul® 3050: 2,2',4,4'-tetrahydroxybenzophenone
Uvinul® M40: 2-hydroxy-4-methoxybenzophenone
Uvinul® 4050H: N,N'-bisformyl-N,N'-bis-(2,2,6,6-tetramethyl-4-piperidinyl)-hexamethylenediamine
Uvinul® A Plus: 2-(4-diethylamino-2-hydroxybenzoyl)-benzoic acid hexyl ester
Uvinul® 3008: 2-hydroxy-4-octyloxybenzophenone
Uvinul® MS 40: 2-hydroxy-4-methoxybenzophenone-5-sulfonic acid
Tinuvin® 770: bis(2,2,6,6-tetramethyl-4-piperidyl)sebacate
Tinuvin® 171: 2-(2H-benzotriazol-2-yl)-6-dodecyl-4-methyl-phenol
Z-Cote®: zinc oxide, micronized Example 1

Preparation of Mixtures

Metaflumizone SC was mixed with a certain amount (in each case wt. % with respect to metaflumizone) of the UV absorber and/or stabilizer, and the mixture was diluted with water in the weight ratio of 1:18 and stirred at room temperature for one hour.

Example 2

Irradiation and Analysis of the Isomerization 20 mg of the mixture prepared in Example 1 were dripped on to a glass plate and left to dry at room temperature for one hour. The sample was then irradiated with UV light (Sun Test CPS+, Atlas Co., 750 watt, wavelength 300 to 800 nm) for 0, 30 or 120 min. After the irradiation the sample was washed off from the glass plate with 2.0 ml of DMSO and homogenized while stirring and by means of ultrasound (15 s). The sample was separated into the E and Z isomers of metaflumizone by means of HPLC (ultra performance liquid chromatography, BEH C18 column, detection at 225 nm) and quantified via the peak areas. The content of E isomer is stated in each case and the content of Z isomer corresponds to 100% minus the content of E isomer.

Example 3

Testing of Various UV Absorbers

The mixtures were prepared as in Example 1 and tested as in Example 2 (Table 1). It was found that the most diverse UV absorbers reduce the E/Z isomerization compared with a mixture which comprises no UV absorber.

TABLE 1

UV absorbers

| UV absorber | Amount[a] | E isomer [%][b] 0 min | E isomer [%][b] 30 min | E isomer [%][b] 120 min |
|---|---|---|---|---|
| — | — | 96 | 58 | 43 |
| Uvitex ® NFW | 60% | 96 | 84 | 83 |
| Uvinul ® 3050 | 60% | 99 | 86 | 76 |
| Uvinul ® M40 | 60% | 99 | 78 | 73 |
| Uvinul ® 4050H | 40% | 98 | 75 | 69 |
| Uvinul ® A Plus | 40% | 97 | 79 | 74 |
| Uvinul ® 3008 | 20% | 97 | 84 | 82 |
| Uvinul ® MS 40 | 40% | 97 | 92 | 82 |

[a] amount with respect to metaflumizone;
[b] content of the E isomer in the total amount of E and Z isomers analyzed.

Example 4

Mixture of UV Absorber with Antioxidants or with Further UV Absorbers

The mixtures were prepared as in Example 1 and tested as in Example 2 (Table 2). It was found that the mixtures of UV absorbers with antioxidants (such as tocopherol, ascorbic acid, Uvinul 4050H, Tinuvin 770) or with further UV absorbers (such as Z-Cote) reduce the E/Z isomerization compared with a mixture which comprises no UV absorber.

TABLE 2

Mixtures

| UV absorber | Amount[a] | E isomer [%][b] 0 min | E isomer [%][b] 30 min | E isomer [%][b] 120 min |
|---|---|---|---|---|
| — | — | 96 | 58 | 43 |
| Uvinul ® MS 40<br>α-Tocopherol | 60<br>10 | 100 | 96 | 92 |
| Uvinul ® MS 40<br>Ascorbic acid | 60<br>10 | 99 | 91 | 80 |
| Uvinul ® MS 40<br>Uvinul 4050H | 60<br>10 | 99 | 89 | 93 |
| Uvinul ® MS 40<br>Tinuvin 770 | 90<br>10 | 97 | 92 | 85 |
| Uvinul ® MS 40<br>Z-Cote ® | 90<br>10 | 98 | 90 | 85 |
| Uvinul ® MS 40<br>Z-Cote ® | 30<br>30 | 97 | 82 | 78 |

[a] amount with respect to metaflumizone;
[b] content of the E isomer in the total amount of E and Z isomers analyzed.

Example 5

Preparation of Suspension Concentrates

An aqueous suspension concentrate of metaflumizone was prepared by mixing and grinding the following components: 180 g/l of metaflumizone, 27 g/l of sodium dioctyl sulfosuccinate, 54 g/l of propylene glycol, 1.1 g/l of xanthan gum, 33 g/l of ethoxylated tristyryiphenol. Water-insoluble UV absorbers or stabilizers were added before the grinding, while water-soluble UV absorbers or stabilizers were added after the grinding and dissolved, while stirring. The amount of UV absorbers or stabilizers has in each case been stated in wt. % with respect to metaflumizone. The particle size was D90<2.0 μm and D50<1.0 μm.

Example 6

Testing of Suspension Concentrates

The suspension concentrates were prepared as in Example 5 and tested as in Example 2 (Table 3). It was found that the results with formulations which were prepared according to Example 5 are as good as the formulations which were prepared by simple mixing in Example 1.

TABLE 3

UV absorbers

| UV absorber | Amount[a] | E isomer [%][b] 0 min | E isomer [%][b] 30 min | E isomer [%][b] 120 min |
|---|---|---|---|---|
| — | — | 96 | 58 | 43 |
| Uvinul ® M 40 | 60% | 94 | 72 | 68 |
| Uvinul ® M 40 | 40% | 94 | 80 | 72 |
| Z-Cote ® | 22% | | | |
| Uvinul ® MS 40 | 60% | 99 | 96 | 92 |
| Uvinul ® MS 40 Ascorbic acid | 60% 15% | 96 | 95 | 91 |

[a] amount with respect to metaflumizone;
[b] content of the E isomer in the total amount of E and Z isomers analyzed.

Example 7

Testing of Diluted Suspension Concentrates

The suspension concentrates were prepared as in Example 5 and tested as in Example 2 (Table 4). The 1:18 dilution with water in Example 2 led to a content of formulation in water of 5%. The content was lowered here still further to 1% by higher dilution with water. This dilution corresponds to a conventional dilution of a commercial active compound concentrate in practice in order to obtain the ready-to-spray tank mix. It was found that the diluted formulations also reduce the E/Z isomerization.

TABLE 4

UV absorbers

| UV absorber | Amount[a] | Content | E isomer [%][b] 0 min | E isomer [%][b] 30 min | E isomer [%][b] 120 min |
|---|---|---|---|---|---|
| — | — | 5% | 96 | 58 | 43 |
| Uvinul ® MS 40 | 60% | 5% | 99 | 96 | 93 |
| Uvinul ® MS 40 | 60% | 1% | 99 | 86 | 76 |
| Uvinul ® MS 40 Ascorbic acid | 60% 15% | 5% | 96 | 95 | 91 |
| Uvinul ® MS 40 Ascorbic acid | 60% 15% | 1% | 96 | 88 | 83 |

[a] amount with respect to metaflumizone;
[b] content of the E isomer in the total amount of E and Z isomers analyzed.

Example 8

Field Trials on White Cabbage

An aqueous suspension concentrate "SC-A" of metaflumizone was prepared by mixing and grinding the following components: 180 g/l metaflumizone, 22 g/l sodium dioctylsulfosuccinate, 35 g/l ethoxylated $C_{9-11}$ alcohol, 30 g/l polyarylphenol ethoxylate, 1 g/l xanthan gum (thickener), and 50 g/l alkanediol (antifreeze agent).

An aqueous suspension concentrate "SC-A+UV1" was prepared from SC-A by addition of 108 g/l Uvinul® MS 40.

An aqueous suspension concentrate "SC-A+UV2" was prepared from SC-A by addition of 25 g/l Uvinul® MS 40.

An aqueous suspension concentrate "SC-A+UV3" was prepared from SC-A by addition of 50 g/l Uvinul® MS 40.

An aqueous suspension concentrate "SC-A+UV4" was prepared from SC-A by addition of 108 g/l Uvitex® NFW.

White cabbage was grown in a test field in the Philippines. The field was sprayed at an application rate of 160 g of metaflumizone per ha. Subsequently, after 14 days, the cumulative feeding damage caused by *Crocidolomia binotalis* was rated (table 5). As a result of the addition of UV absorber, the active ingredient had a higher activity for longer.

TABLE 5

| | Cumulative feeding damage [%] |
|---|---|
| SC-A | 123 |
| SC-A + UV1 | 98 |

Example 9

Field Trials on White Cabbage

White cabbage was grown in a test field in California. The field was sprayed at an application rate of 160 g of metaflumizone per ha, using the suspension concentrates in accordance with example 8. Subsequently, after 14 days, the mortality of the larvae of *Lepidoptera* was ascertained (Table 6). As a result of the addition of UV absorber, the active ingredient had a higher activity for longer.

TABLE 6

| | Mortality [%] |
|---|---|
| SC-A | 41 |
| SC-A + UV1 | 70 |

Example 10

Field Trials on Potatoes

Potatoes were grown on a test field in North Carolina (USA) (plots 7*1 m, three plots per trial point). The field was sprayed with an application rate of 60 g of metaflumizone per ha, using the suspension concentrates corresponding to example 8. Subsequently, after 19 days, the number of the larvae of *Leptinotarsa decemlineata* (in all larval stages) and their feeding damage were ascertained (table 7). As a result of the addition of UV absorber, the active ingredient had a higher activity for longer.

TABLE 7

| | Number of larvae | Feeding damage [%] |
|---|---|---|
| No treatment | 150 | 58 |
| SC-A | 105 | 32 |
| SC-A + UV1 | 22 | 15 |
| SC-A + UV2 | 12 | 10 |

Example 11

UV Chamber, Lima Beans

Lima beans at the growth stage with the first leaves were sprayed with 30 g of metaflumizone per ha in a laboratory spraying chamber. The plants were then transferred to a growth chamber with UV light and fluorescent light, with irradiation for 24 h/day. After 3, 10, 14, and 17 days (DAT), leaves were removed and placed in Petri dishes together with a moist piece of filter paper. Added to each dish were 5 *Spodoptera eridania* (Southern Armyworm; larval stage 3). For each trial, four replications were carried out. The cumulative feeding damage is summarized in table 8.

TABLE 8

|  | Feeding damage [%] |
| --- | --- |
| SC-A | 97 |
| SC-A + UV1 | 58 |
| SC-A + UV2 | 52 |
| SC-A + UV3 | 61 |

Example 12

Field Trials on Potatoes

Potatoes were grown on a test field in North Carolina (USA) (plots 7*1 m, three plots per trial point). The field was sprayed with an application rate of 30 or 60 g of metaflumizone per ha, using the suspension concentrates corresponding to example 8. Subsequently, after 19 days, the number of the larvae of *Leptinotarsa decemlineata* (in all larval stages) were ascertained (table 9). As a result of the addition of UV absorber, the active ingredient had a higher activity for longer.

TABLE 9

| | Average number of larvae per plot | |
| --- | --- | --- |
| | 30 g metaflumizone/ha | 60 g metaflumizone/ha |
| No treatment | 150 | 150 |
| SC-A | 145 | 105 |
| SC-A + UV1 | 37 | 22 |
| SC-A + UV2 | 27 | 12 |
| SC-A + UV4 | 123 | 61 |

The invention claimed is:

1. A composition comprising metaflumizone and a UV absorber comprising a sulfonic acid group wherein the E isomer of metaflumizone is present in an amount to at least 90 wt. %, based on the total amount of the E and Z isomers of metaflumizone, wherein the UV absorber is a sulfonic acid derivative of benzophenone having a solubility in water at 20° C. of at least 5.0 g/l; and wherein the UV absorber is present in an amount that is sufficient to effectively reduce the E/Z isomerization of metaflumizone.

2. The composition according to claim 1, comprising a further UV absorber, the further UV absorber being oil-soluble.

3. A method of controlling phytopathogenic fungi or undesirable insect or mite infestation, comprising applying the composition according to claim 1 to the fungi or undesirable insects or mites, their habitat, and/or plants or soil to be protected from the fungi or undesirable insects or mite infestation.

4. The method of claim 3, wherein the amount of the UV absorber is 0.5 to 500 wt. % with respect to the amount of metaflumizone.

5. The method of claim 3, wherein an antioxidizing agent is used in addition to the UV absorber.

6. The method of claim 5, wherein the weight ratio of UV absorber to antioxidizing agent is in the range of from 1/10 to 10/1.

* * * * *